United States Patent
Stephens et al.

(10) Patent No.: US 7,166,276 B2
(45) Date of Patent: Jan. 23, 2007

(54) SILICONE ELASTOMER EMULSION COSMETIC COMPOSITION COMPRISING COLORANT INCLUSIVE INTERNAL PHASE

(75) Inventors: Alison Fiona Stephens, Cookham (GB); Neil John Jones, Staines (GB); Jorge Max Sunkel, Cincinnati, OH (US); Michael Lee Vatter, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 101 days.

(21) Appl. No.: 10/280,525

(22) Filed: Oct. 25, 2002

(65) Prior Publication Data
US 2003/0108498 A1 Jun. 12, 2003

(30) Foreign Application Priority Data
Oct. 26, 2001 (GB) ................ 0125778.1

(51) Int. Cl.
| A61K 8/18 | (2006.01) |
|---|---|
| A61K 8/00 | (2006.01) |
| A61K 8/81 | (2006.01) |
| A61K 8/92 | (2006.01) |
| A61K 8/02 | (2006.01) |

(52) U.S. Cl. ................ 424/63; 424/59; 424/64; 424/70.6; 424/70.7; 424/400; 424/401; 424/DIG. 5; 514/845; 514/938; 514/941

(58) Field of Classification Search ........... 424/400, 424/401, 59, 65, 64, 70.6, 70.7, DIG. 5; 514/845, 514/938, 941
See application file for complete search history.

(56) References Cited

U.S. PATENT DOCUMENTS

| | | | |
|---|---|---|---|
| 3,843,601 A | 10/1974 | Bruner | |
| 4,554,369 A | 11/1985 | Hill et al. | |
| 4,588,617 A | 5/1986 | Oka | |
| 4,720,353 A | 1/1988 | Bell | |
| 4,742,142 A | 5/1988 | Shimizu et al. | |
| 4,746,513 A | 5/1988 | Smith | |
| 4,752,528 A | 6/1988 | Oka | |
| 4,761,454 A | 8/1988 | Oba et al. | |
| 4,780,145 A | 10/1988 | Mori et al. | |
| 4,814,184 A | 3/1989 | Aguadisch et al. | |
| 4,970,252 A | 11/1990 | Sakuta et al. | |
| 4,980,167 A | 12/1990 | Harashima et al. | |
| 4,983,388 A | 1/1991 | Kuwata et al. | |
| 4,987,169 A | 1/1991 | Kuwata et al. | |
| 5,035,890 A | 7/1991 | Braun | |
| 5,128,431 A | 7/1992 | Riding et al. | |
| 5,143,722 A | 9/1992 | Hollenberg et al. | |
| 5,220,033 A | 6/1993 | Kamei et al. | |
| 5,236,986 A | 8/1993 | Sakuta | |
| 5,266,321 A | 11/1993 | Shukuzaki et al. | |
| 5,280,019 A | 1/1994 | Kllimisch | |
| 5,330,747 A | 7/1994 | Krzysik | |
| 5,356,627 A * | 10/1994 | Da Cunha et al. ......... 424/401 |
| 5,387,417 A | 2/1995 | Rentsch | |
| 5,399,342 A | 3/1995 | Krzysik | |
| 5,403,580 A | 4/1995 | Bujanowski et al. | |
| 5,412,004 A | 5/1995 | Tachibana et al. | |
| 5,512,272 A | 4/1996 | Krzysik | |
| 5,599,533 A | 2/1997 | Stepniewski et al. | |
| 5,628,989 A | 5/1997 | Harashima et al. | |
| 5,654,362 A | 8/1997 | Schulz, Jr. et al. | |
| 5,665,804 A | 9/1997 | Hill et al. | |
| 5,686,602 A | 11/1997 | Farooq et al. | |
| 5,721,026 A | 2/1998 | Feder et al. | |
| 5,725,845 A | 3/1998 | Krog et al. | |
| 5,726,138 A | 3/1998 | Tsaur et al. | |
| 5,726,456 A | 3/1998 | Lupton et al. | |
| 5,750,123 A | 5/1998 | Znaiden et al. | |
| 5,756,568 A | 5/1998 | Morita et al. | |
| 5,760,116 A | 6/1998 | Kilgour et al. | |
| 5,811,487 A | 9/1998 | Schulz, Jr. et al. | |
| 5,833,973 A | 11/1998 | Dobkowski et al. | |
| 5,837,793 A | 11/1998 | Harashima et al. | |
| 5,849,314 A | 12/1998 | Dobkowski et al. | |
| 5,853,711 A | 12/1998 | Nakamura et al. | |
| 5,853,741 A | 12/1998 | Znaiden et al. | |

(Continued)

FOREIGN PATENT DOCUMENTS

CA 1319306 6/1992

(Continued)

*Primary Examiner*—Sreeni Padmanabhan
*Assistant Examiner*—Marina Lamm
(74) *Attorney, Agent, or Firm*—Vladimir Virenberg; Kenya T. Pierre; Dara M. Kendall

(57) ABSTRACT

The present invention relates to silicone elastomer emulsion cosmetic compositions that comprise an internal phase the further includes a colorant. These compositions are intended to deliver such colorant ingredients to the skin of the user in such a manner as to provide a smooth and even colored appearance. In particular, the present invention relates to a cosmetic composition comprising an emulsion that further comprises:

a) a continuous aqueous phase comprising:
  1) from about 0.1% to about 10%, by weight of the composition, of a non-emulsifying crosslinked siloxane elastomer;
b) a dispersed oil phase comprising:
  1) from about 1% to about 25%, by weight of the composition, of an oil compatible colorant; and
  2) from about 0.01% to about 20%, by weight of the composition, of a binder; and
c) from about 0.01% to about 15%, by weight of the composition, of an emulsifier.

10 Claims, No Drawings

U.S. PATENT DOCUMENTS

| | | |
|---|---|---|
| 5,854,336 A | 12/1998 | Divone, Sr. et al. |
| 5,859,069 A | 1/1999 | Yanagida |
| 5,871,722 A | 2/1999 | Lupton et al. |
| 5,871,761 A | 2/1999 | Kuwata et al. |
| 5,880,210 A | 3/1999 | Schulz, Jr. et al. |
| 5,889,108 A | 3/1999 | Zhang |
| 5,919,437 A | 7/1999 | Lee et al. |
| 5,919,468 A | 7/1999 | Bara |
| 5,922,308 A | 7/1999 | Brewster et al. |
| 5,929,164 A | 7/1999 | Zhang |
| 5,939,478 A | 8/1999 | Beck et al. |
| 5,942,215 A | 8/1999 | Edwards et al. |
| 5,945,471 A | 8/1999 | Morita et al. |
| 5,948,855 A | 9/1999 | Lin et al. |
| 5,969,035 A | 10/1999 | Meinhardt et al. |
| 5,972,314 A * | 10/1999 | Crotty et al. .................. 424/59 |
| 5,977,280 A | 11/1999 | Kadlec et al. |
| 5,985,807 A | 11/1999 | Auguste et al. |
| 5,998,542 A | 12/1999 | Horne et al. |
| 6,013,247 A | 1/2000 | Bara et al. |
| 6,024,944 A | 2/2000 | Hansenne |
| 6,027,738 A | 2/2000 | Stepniewski et al. |
| 6,039,935 A * | 3/2000 | Mohammadi ................. 424/59 |
| 6,066,727 A | 5/2000 | Yamamoto et al. |
| 6,074,672 A | 6/2000 | Dobkowski et al. |
| 6,080,394 A | 6/2000 | Lin et al. |
| 6,083,900 A | 7/2000 | Auguste et al. |
| 6,103,250 A | 8/2000 | Brieva et al. |
| 6,168,782 B1 | 1/2001 | Lin et al. |
| 6,261,713 B1 | 7/2001 | Walele et al. |
| 6,264,934 B1 | 7/2001 | Kantner et al. |
| 6,511,657 B2 | 1/2003 | Avendano et al. |
| 6,518,228 B1 | 2/2003 | Jorgensen et al. |
| 6,538,061 B2 | 3/2003 | Chaiyawat et al. |
| 6,565,862 B1 * | 5/2003 | Bara ......................... 424/401 |
| 6,566,406 B1 | 5/2003 | Pathak et al. |
| 6,638,519 B1 * | 10/2003 | Lorant ........................ 424/401 |
| 6,743,830 B2 | 6/2004 | Soane et al. |
| 2001/0041768 A1 | 11/2001 | Lorant |
| 2003/0138490 A1 | 7/2003 | Hu et al. |

FOREIGN PATENT DOCUMENTS

| | | |
|---|---|---|
| EP | 0 295886 A2 | 12/1988 |
| EP | 0 499398 A2 | 8/1992 |
| EP | 0 542498 A2 | 5/1993 |
| EP | 0 545002 A1 | 6/1993 |
| EP | 0 608989 A2 | 8/1994 |
| EP | 0 796883 A2 | 9/1997 |
| EP | 0 829253 A2 | 3/1998 |
| EP | 0 848029 A2 | 6/1998 |
| EP | 0 850643 A1 | 7/1998 |
| EP | 0 855178 A2 | 7/1998 |
| EP | 0 882753 A1 | 9/1998 |
| EP | 0 908175 A1 | 4/1999 |
| EP | 0 917 870 A1 * | 5/1999 |
| EP | 0 917870 A1 | 5/1999 |
| EP | 0 934959 A1 | 8/1999 |
| EP | 0 958856 A1 | 11/1999 |
| EP | 0 972512 A1 | 1/2000 |
| EP | 0 985402 A1 | 3/2000 |
| EP | 1 010715 A1 | 6/2000 |
| EP | 1 020 494 A1 | 7/2000 |
| EP | 1 048 686 A2 | 11/2000 |
| EP | 1 057 872 A1 | 12/2000 |
| EP | 1 062944 A1 | 12/2000 |
| EP | 1 064930 A1 | 1/2001 |
| EP | 1 068852 A1 | 1/2001 |
| EP | 0 779322 B1 | 2/2001 |
| EP | 1 095959 A2 | 5/2001 |
| EP | 1 097968 A1 | 5/2001 |
| EP | 1 164171 A2 | 12/2001 |
| FR | 2 768 926 | 4/1999 |
| FR | 2 779440 A1 | 12/1999 |
| JP | SHO 61-194009 | 8/1986 |
| JP | HEI 1-207354 | 8/1989 |
| JP | HEI 4-017162 | 3/1992 |
| JP | KOKAI 5-139929 | 6/1993 |
| JP | 5-178733 | 7/1993 |
| JP | 5-178734 | 7/1993 |
| JP | 6-072826 | 3/1994 |
| JP | 7-258027 | 10/1995 |
| JP | 7-277924 | 10/1995 |
| JP | 8-259419 | 10/1996 |
| JP | 8-295620 | 11/1996 |
| JP | 8-319215 | 12/1996 |
| JP | 8-319218 | 12/1996 |
| JP | 9-067233 | 3/1997 |
| JP | 9-136813 | 5/1997 |
| JP | 9-151126 | 6/1997 |
| JP | 9-175939 | 7/1997 |
| JP | 9-175940 | 7/1997 |
| JP | 9-175990 | 7/1997 |
| JP | 9-301825 | 11/1997 |
| JP | 9-315936 | 12/1997 |
| JP | 9-323917 | 12/1997 |
| JP | 9-328409 | 12/1997 |
| JP | 10-045536 | 2/1998 |
| JP | 10-120525 | 5/1998 |
| JP | 10-130120 | 5/1998 |
| JP | 10-167925 | 6/1998 |
| JP | 10-182354 | 7/1998 |
| JP | 10-236917 | 9/1998 |
| JP | 11-021227 | 1/1999 |
| JP | 11-029436 | 2/1999 |
| JP | 11-071236 | 3/1999 |
| JP | 11-092335 | 4/1999 |
| JP | 11-158036 | 6/1999 |
| JP | 11-180847 | 7/1999 |
| JP | 11-193214 | 7/1999 |
| JP | 2000-007549 | 1/2000 |
| JP | 2000-103717 | 4/2000 |
| JP | 2000-226316 | 8/2000 |
| WO | WO 96/18374 A1 | 6/1996 |
| WO | WO 96/29979 A1 | 10/1996 |
| WO | WO 97/44010 A1 | 11/1997 |
| WO | WO 98/00098 A1 | 1/1998 |
| WO | WO 98/00102 A1 | 1/1998 |
| WO | WO 98/00103 A1 | 1/1998 |
| WO | WO 98/00104 A1 | 1/1998 |
| WO | WO 98/00105 A1 | 1/1998 |
| WO | WO 98/42307 A1 | 10/1998 |
| WO | WO 99/00400 A1 | 1/1999 |
| WO | WO 99/13859 A1 | 3/1999 |
| WO | WO 99/22696 A1 | 5/1999 |
| WO | WO 99/43297 A2 | 9/1999 |
| WO | WO 99/51192 A2 | 10/1999 |
| WO | WO 99/63953 A1 | 12/1999 |
| WO | WO 00/21493 A1 | 4/2000 |
| WO | WO 00/61076 A1 | 10/2000 |
| WO | WO 00/61084 A1 | 10/2000 |
| WO | WO 00/72817 A1 | 12/2000 |
| WO | WO 01/12133 A2 | 2/2001 |
| WO | WO 01/14458 A1 | 3/2001 |
| WO | WO 200292047 A1 * | 11/2002 |

* cited by examiner

SILICONE ELASTOMER EMULSION COSMETIC COMPOSITION COMPRISING COLORANT INCLUSIVE INTERNAL PHASE

FIELD OF INVENTION

The present invention relates to silicone elastomer emulsion cosmetic compositions that comprise an internal phase the further includes a colorant. These compositions are intended to deliver such colorant ingredients to the skin of the user in such a manner as to provide a smooth and even colored appearance while actually providing discontinuous coverage.

BACKGROUND

A typical problem experienced in the application of cosmetics to the skin is the difficulty associated with controlling the deposition of the colorants included therein, particularly pigments. This lack of controlled deposition usually results in uneven application of the cosmetic such that either a cakey appearance or an uneven, blotchy look is achieved. It is generally believed that such undesirable effects come from the random dispersion of the colorant materials in the composition. Oftentimes, these materials agglomerate within the cosmetic and cause clumping while packaged as well as upon application to the skin.

Applicants, however, have found a solution to the above-mentioned agglomeration problem that accompanies the use of numerous cosmetics. Applicants have found that the inclusion of colorant materials in the internal phase of a silicone elastomer-containing emulsion-type cosmetic allows for not only smooth application but a discontinuous although even appearing product coverage Additional advantages of these compositions include a soft, smooth feel and good application.

SUMMARY OF THE INVENTION

The present invention relates to a cosmetic composition comprising an emulsion that further comprises:
a) a continuous oil phase comprising
  1) from about 0.1% to about 10%, by weight of the composition, of a non-emulsifying crosslinked siloxane elastomer; and
  2) from about 10% to about 90%, by weight of the composition, of a solvent for the elastomer;
b) a dispersed aqeuous phase comprising:
  1) from about 1% to about 25%, by weight of the composition, of an aqueous compatible colorant;
  2) from about 0.01% to about 20%, by weight of the composition, of a binder; and
  3) from about 1% to about 95%, by weight of the composition, of water; and
c) from about 0.01% to about 15%, by weight of the composition, of an emulsifier.

Another aspect of the invention relates to a cosmetic composition comprising an emulsion that further comprises:
a) a continuous aqueous phase comprising:
  1) from about 0.1% to about 10%, by weight of the composition, of a non-emulsifying crosslinked siloxane elastomer; and
  2) from about 1% to about 95, by weight of the composition, of water; and b) a dispersed oil phase comprising:
  1) from about 1% to about 25%, by weight of the composition, of an oil compatible colorant; and
  2) from about 0.01% to about 20%, by weight of the composition, of a binder; and
c) from about 0.01% to about 15%, by weight of the composition, of an emulsifier.

DETAILED DESCRIPTION OF THE INVENTION

As used herein, "comprising" means that other steps and ingredients can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

As used herein, the term "cosmetics" includes make-up, foundation, and other skin care products. The term "make-up" refers to products that leave color on the face, including foundation, blacks and browns, i.e., mascaras, concealers, eye liners, brow colors, eye shadows, blushers, lip colors, powders, solid emulsion compacts, and so forth. "Skin care products" are those used to treat or care for, or somehow moisturize, improve, or clean the skin. Products contemplated by the phrase "skin care products" include, but are not limited to, adhesives, bandages, toothpaste, anhydrous occlusive moisturizers, antiperspirants, deodorants, personal cleansing products, powder laundry detergent, fabric softener towels, occlusive drug delivery patches, nail polish, powders, tissues, wipes, hair conditioners-anhydrous, shaving creams and the like. The term "foundation" refers to liquid, creme, mousse, pancake, compact, concealer or like products created or reintroduced by cosmetic companies to even out the overall coloring of the skin. Foundation is manufactured to work better over moisturized and/or oiled skin. As used herein, "excess moisture" or "excessive moisture" means an undesirable and/or unhealthy level of bodily fluids deposited on human skin.

The term "ambient conditions" as used herein refers to surrounding conditions under about one atmosphere of pressure, at about 50% relative humidity, and at about 25° C., unless otherwise specified.

Unless otherwise indicated, all percentages and ratios used herein are by weight of the total composition. All weight percentages, unless otherwise indicated, are on an actives weight basis. All measurements made are at 25° C., unless otherwise designated.

Emulsion

The cosmetic compositions of the present invention are in the form of emulsions. Suitable emulsions include but are not limited to water-in-oil emulsions, water-in-silicone emulsions, oil-in water emulsions, silicone-in-water emulsions, and like emulsions. Preferred emulsions of the present invention include water-in-oil emulsions. Depending on the nature of the particular emulsion, it will contain either a continuous oil phase and a dispersed aqueous phase or a continuous aqueous phase and a dispersed oil phase. As used herein, the oil phase may include hydrocarbon oil based phases as well as silicone oil based phases.

Non-Emulsifying Crosslinked Siloxane Elastomer

The compositions of the present invention comprise a non-emulsifying crosslinked organopolysiloxane elastomer in the oil phase, whether such phase is the dispersed phase or the continuous phase. The term "non-emulsifying," as used herein, defines crosslinked organopolysiloxane elastomer from which polyoxyalkylene units are absent. No specific restriction exists as to the type of curable organopolysiloxane composition, which can serve as the starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane; condensation-curing organopolysiloxane compositions which cure in the presence of an organotin compound or a titanate ester, by a condensation reaction between an hydroxyl-terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;

(B) an organopolysiloxane having at least 2 silicon-bonded hydrogen atoms in each molecule; and (C) a platinum-type catalyst.

With regard to the above, component (A) is the basic component of the silicone elastomer-generating organopolysiloxane, and curing proceeds by the addition reaction of this component with component (B) under catalysis by component (C). This component (A) must contain at least 2 silicon-bonded lower alkenyl groups in each molecule; an excellent cured product will not be obtained at fewer than two lower alkenyl groups because a network structure will not be formed. Said lower alkenyl groups are exemplified by vinyl, allyl, and propenyl. While the lower alkenyl groups can be present at any position in the molecule, their presence at the molecular terminals is preferred. The molecular structure of this component may be straight chain, branched straight chain, cyclic, or network, but a straight chain, possibly slightly branched, is preferred. The molecular weight of the component is not specifically restricted, and thus the viscosity may range from low viscosity liquids to very high viscosity gums. In order for the cured product to be obtained in the form of the rubbery elastomer, it is preferred that the viscosity at 25° C. be at least 100 centistokes. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers.

Component (B) is an organopolysiloxane having at least 2 silicon-bonded hydrogen atoms in each molecule and is a crosslinker for component (A). Curing proceeds by the addition reaction of the silicon-bonded hydrogen atoms in this component with the lower alkenyl groups in component (A) under catalysis by component (C). This component (B) must contain at least 2 silicon-bonded hydrogen atoms in each molecule in order to function as a crosslinker. Furthermore, the sum of the number of alkenyl groups in each molecule of component (A) and the number of silicon-bonded hydrogen atoms in each molecule of component (B) is to be at least 5. Values below 5 should be avoided because a network structure is then essentially not formed.

No specific restriction exists on the molecular structure of this component, and it may be any of straight chain, branch-containing straight chain, cyclic, etc. The molecular weight of this component is not specifically restricted, but it is preferred that the viscosity at 25° C. be 1 to 50,000 centistokes in order to obtain good miscibility with component (A). It is preferred that this component be added in a quantity such that the molar ratio between the total quantity of silicon-bonded hydrogen atoms in the instant component and the total quantity of all lower alkenyl groups in component (A) falls within the range of 1.5:1 to 20:1. It is difficult to obtain good curing properties when this molar ratio falls below 0.5:1. When 20:1 is exceeded, there is a tendency for the hardness to increase to high levels when the cured product is heated. Furthermore, when an organosiloxane containing substantial alkenyl is supplementarily added for the purpose of; for example, reinforcement, it is preferred that a supplemental addition of the instant SiH-containing component be made in a quantity offsetting these alkenyl groups. This component is concretely exemplified by trimethylsiloxy-terminated methylhydrogenpolysiloxanes, trimethylsiloxy-terminated dimethylsiloxane-methylhydrogensiloxane copolymers, and dimethylsiloxane-methylhydrogen-siloxane cyclic copolymers.

Component (C) is a catalyst of the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

This component is added preferably at 0.1 to 1,000 weight parts, and more preferably at 1 to 100 weight parts, as platinum-type metal proper per 1,000,000 weight parts of the total quantity of components (A) plus (B). Other organic groups which may be bonded to silicon in the organopolysiloxane forming the basis for the above-described curable organopolysiloxane compositions are, for example, alkyl groups such as methyl, ethyl, propyl, butyl, and octyl; substituted alkyl groups such as 2-phenylethyl, 2-phenylpropyl, and 3,3,3-trifluoropropyl; aryl groups such as phenyl, tolyl, and xylyl; substituted aryl groups such as phenylethyl; and monovalent hydrocarbon groups substituted by, for example, the epoxy group, the carboxylate ester group, the mercapto group, etc.

Examples of the production of the organopolysiloxane elastomer powder are as follows:

an organopolysiloxane composition as described above (additional-curable, condensation-curable, or peroxide-curable)

is mixed with water in the presence of a surfactant (nonionic, anionic, cationic, or amphoteric), and, after mixing to homogeneity in a homomixer, colloid mill, homogenizer, propeller mixer, etc., this is cured by discharge into hot water (temperature at least 50° C.) and is then dried; the organopolysiloxane composition (addition-curable, condensation-curable, or peroxide-curable) is cured by spraying it directly into a heated current; the powder is obtained by curing a radiation-curable organopolysiloxane composition by spraying it under high energy radiation; the organopolysiloxane composition (addition-curable, condensation-curable, peroxide-curable) or high energy-curable organopolysiloxane composition is cured, the latter by high energy radiation, and the product is then pulverized using a known pulverizer such as, for example, a ball mill, atomizer, kneader, roll mill, etc., to thereby form the powder. Suitable organopolysiloxane elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200, and hybrid silicone powders that contain a phenyl group such as Shin-Etsu's KSP-300; and Dow Corning's DC 9506.

Preferred organopolysiloxane compositions are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), Grant Industries (Gransil™ line of materials), and lauryl dimethicone/vinyl dimethicone crosspolymers supplied by Shin Etsu (e.g., KSG-31, KSG-32, KSG-41, KSG-42, KSG-43, and KSG-44). Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK.

The non-emulsifying cross-linked organopolysiloxane elastomers of the present invention are preferably further processed by subjecting them to a high shear (approximately 5,000 psi) treatment in the presence of a solvent for the siloxane elastomer via a Sonolator at less than 10 passes. Sonolation achieves a resultant composition with elastomer average particle size ranging from at least 20 (or about 20) microns to about 200 microns, preferably from about 30 to about 150 microns, more preferably from 40 (or about 40) to about 95 microns and most preferably from about 50 microns to about 90 microns as measured by the Horiba LA-910 (described below). As used herein, the term "particle size" of the elastomer represents the elastomer particle size in its swelled state. By "swelled," as used herein, means that the elastomer particles have extended beyond their normal size and shape by virtue of their absorption of the solvent compound. Viscosity is best when ranging between above 20,000 (or above about 20,000) and about 6,000,000, preferably from about 25,000 to about 4,000,000, more preferably from about 30,000 to about 3,000,000, most preferably from about 40,000 to about 2,000,000, optimally about 60,000 to about 1,500,000 cps at 25° C. as measured by a Brookfield LV Viscometer (size 4 bar, 60 rpm, 0.3 sec.).

Without being limited by theory, it is believed that compositions incorporating non-emulsifying elastomer/solvent gels that include non-emulsifying cross-linked organopolysiloxane elastomers having an average particle size greater than 10 microns (or greater than about 10 microns) and/or viscosities greater than 20,000 cps provide films that exhibit improved smoothness, uniformity and evenness of particle (e.g., pigments) distribution within the film (i.e., solid particles remain distributed within and throughout the film as opposed to such particles protruding from the film into and/or across the film/air interface).

Preferably, the non-emulsifying cross-linked organopolysiloxane elastomers do not undergo recycled processing. Without being limited by theory, recycled processing produces broad particle size distributions comprising particles larger or smaller than that necessary to achieve the skin feel benefits of the present invention. Specifically, gel balls often result from silicone elastomer particles larger than 200 microns while elastomer particles smaller than 10 microns reduce skin feel and viscosity benefits. Such particle size distributions result from a failure to ensure that all of the elastomer particle materials experience the same shear throughout the process. Typically, with recycling, only a portion of the particles experience shear before these sheared particles are returned to the process starting point and combined with the remaining un-sheared particles. Similarly, the next cycle begins with only a portion of this particle mixture experiencing before the newly sheared mixture particles are returned to the process starting point and combined with the remaining un-sheared particle mixture. Importantly, even after considerable recycling, some of the particles never actually experience shear while others experience a high degree of shear. The result is a particle size range, which encompasses particles both larger and smaller than those necessary to achieve the present invention.

In contrast, discrete pass processing, as alluded to above, ensures that all the particles experience shear as well as the same amount of shear with each run or pass. More specifically, no run or pass is completed until all the particles have experienced the same shear force. Consequently, the particle size distribution is narrower than that produced by "recycling" with respect to specific particle sizes. This results in a better balance between gel ball formation and viscosity as well as skin feel and viscosity. Additionally preferred non-emulsifying crosslinked organopolysiloxane elastomers are water dispersible spherical powders produced as aqueous dispersions. These elastomers are cured silicone rubbers having particle sizes in the range of 0.1–100 microns. The powder is dispersed in an aqueous medium containing a surface active agent (i.e., emulsifier) to ensure hydrophilicity. The material can be prepared by in-situ crosslinkling in a mixture consisting of an alkenyl containing diroganopolysiloxane and an organohyrdogenpolysiloxane jointly emulsified in an aqueous medium in the presence of a surface active agent. The mechanism for the crosslinking is a hydrosilation reaction between the alkenyl groups and in the alkenyl containing diorganopolysiloxane and the silicone bonded hydrogen atoms in the organohydrogenpolysiloxane in the presence of a platinum compound acting as a catalyst for the hydrosilation reaction. These materials are available commercially from Shin Etsu and are described in detail in U.S. Pat. No. 5,871,761. A similar material is available from Dow Corning as a non-ionic suspension of dimethicone/vinyidimethicone crosspolymer (available as DC9509).

The non-emulsifying crosslinked organopolysiloxane elastomer is present in the compositions of the present invention at concentrations of from about 0.1 to about 10%, optimally from about 1 to about 10%, most preferably from about 2 to about 4% by weight.

Solvent for the Non-Emulsifying Crosslinked Siloxane Elastomer

The compositions of the present invention comprise a solvent for the crosslinked organopolysiloxane elastomer described above. The solvent, when combined with the cross-linked organopolysiloxane elastomer particles of the present invention, serves to suspend and swell the elastomer particles to provide an elastic, gel-like network or matrix. The solvent for the cross-linked siloxane elastomer is liquid under ambient conditions, and preferably has a low viscosity to provide for improved spreading on the skin.

Concentrations of the solvent in the cosmetic compositions of the present invention will vary primarily with the type and amount of solvent and the cross-linked siloxane elastomer employed. Preferred concentrations of the solvent are from about 10% to about 90%, preferably from about 20% to about 80%, more preferably from about 30% to about 70%, by weight of the composition.

The solvent for the cross-linked siloxane elastomer comprises one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The solvent for the cross-linked siloxane elastomer preferably has a solubility parameter of from about 3 to about 13 $(cal/cm^3)^{0.5}$, more preferably from about 5 to about 11 $(cal/cm^3)^{0.5}$, most preferably from about 5 to about 9 $(cal/cm^3)^{0.5}$. Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988.

The solvent preferably includes volatile, non-polar oils; non-volatile, relatively polar oils; non-volatile, non-polar oils; and non-volatile paraffinic hydrocarbon oils, each discussed more fully hereinafter. The term "non-volatile" as used herein refers to materials which exhibit a vapor pressure of no more than about 0.2 mm Hg at 25° C. at one atmosphere and/or to materials that have a boiling point at one atmosphere of at least about 300° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 $(cal/cm^3)^{0.5}$.

1. Non-Polar, Volatile Oils

The non-polar, volatile oil tends to impart highly desirable aesthetic properties to the compositions of the present invention. Consequently, the non-polar, volatile oils are preferably utilized at fairly high levels. Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27–104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include polydecanes such as isododecane and isodecane (e.g., Permethyl-99A which is available from Presperse Inc.) and the C7–C8 through C12–C15 isoparaffins (such as the Isopar Series available from Exxon Chemicals). Non-polar, volatile liquid silicone oils are disclosed in U.S. Pat. No. 4,781,917 issued to Luebbe et al. on Nov. 1, 1988. Additionally, a description of various volatile silicones materials is found in Todd et al., "Volatile Silicone Fluids for Cosmetics", Cosmetics and Toiletries, 91:27–32 (1976). Particularly preferred volatile silicone oils are selected from the group consisting of cyclic volatile silicones corresponding to the formula:

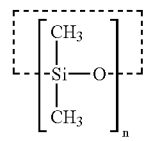

wherein n is from about 3 to about 7; and linear volatile silicones corresponding to the formula:

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

2. Relatively Polar, Non-Volatile Oils

The non-volatile oil is "relatively polar" versus the non-polar, volatile oil discussed above. Therefore, the non-volatile co-solvent is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. Preferably, relatively polar, non-volatile oils useful in the present invention are selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain alicyclic or aromatic rings. More preferably, the relatively polar, non-volatile liquid co-solvent is selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof. More preferred are propoxylated ethers of C14–C18 fatty alcohols having a degree of propoxylation below about 50, esters of C2–C8 alcohols and C12–C26 carboxylic acids (e.g. ethyl myristate, isopropyl palmitate), esters of C12–C26 alcohols and benzoic acid (e.g., Finsolv TN supplied by Finetex), diesters of C2–C8 alcohols and adipic, sebacic, and phthalic acids (e.g., diisopropyl sebacate, diisopropyl adipate, di-n-butyl phthalate), polyhydric alcohol esters of C6–C26 carboxylic acids (e.g., propylene glycol dicaprate/dicaprylate, propylene glycol isostearate); and mixtures thereof. Even more preferred are branched-chain aliphatic fatty alcohols having from about 12–26 carbon atoms. Even more preferred are isocetyl alcohol, octyldecanol, octyldodecanol and undecylpentadecanol; and most preferred is octyidodecanol. Such preferred aliphatic fatty alcohols are particularly useful in combination with the volatile liquid silicone oils discussed herein to adjust the average solubility of the solvent.

3. Non-Polar, Non-Volatile Oils

In addition to the liquids discussed above, the solvent for the cross-linked siloxane elastomer may optionally include non-volatile, non-polar oils. Typical non-volatile, non-polar emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. The non-volatile oils useful in the present invention are essentially non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 1 to about 100,000 centistokes at 25° C. Among the preferred non-volatile silicone emollients useful in the present compositions are the polydimethyl siloxanes having viscosities from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991. Preferred mineral oils have the following properties:

(1) viscosity from about 5 centistokes to about 70 centistokes at 40° C.;
(2) density between about 0.82 and 0.89 g/cm3 at 25° C.;
(3) flash point between about 138° C. and about 216° C.; and
(4) carbon chain length between about 14 and about 40 carbon atoms.

Preferred branched chain hydrocarbon oils have the following properties:

(1) density between about 0.79 and about 0.89 g/cm3 at 20° C.
(2) boiling point greater than about 250° C.; and
(3) flash point between about 110° C. and about 200° C.

Particularly preferred branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

Additional solvents useful herein are described in U.S. Pat. No. 5,750,096 to Gerald J. Guskey et al., issued May 12, 1998.

Aqueous Compatible & Oil Compatible Colorants

The present compositions comprise from about 1% to about 25%, preferably from about 10% to about 20%, more preferably from about 12% to about 19% and most preferably from about 14% to about 18%, each by weight of the composition, of a colorant. Depending on the compatibility of the colorant, it may be included in either the aqueous phase or the oil phase.

With regard to the oil compatible colorants, there are no specific limitations as to the pigment, colorant or filler powders that can be used in the composition. Each may be a body pigment, inorganic white pigment, inorganic colored pigment, pearling agent, and the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, to El-Nokaly et al., issued Nov. 18, 1997. These pigments and powders can be used independently or in combination.

Also useful herein are pigment and/or dye encapsulates such nanocolorants from BASF and multi-layer interference pigments such as Sicopearls from BASF.

It is preferred that the oil compatible colorants, whether they be pigments/powders, be surface treated to provide added stability of color and ease of formulation. Hydrophobically treated pigments are more preferred, because they may be more easily dispersed in the solvent/oil phase. In addition, it may be useful to treat the pigments with a material that is compatible with a silicone phase. Particularly useful hydrophobic pigment treatments for use in water-in-silicone emulsions include polysiloxane treatments such as those disclosed in U.S. Pat. No. 5,143,722. Also preferred are pigment/powders having a primary average particle size of from about 5 nm to about 100,000 nm, more preferably from about 50 nm to about 5,000 nm, most preferably from about 100 nm to about 1000 nm. Mixtures of the same or different pigment/powder having different particle sizes are also useful herein (e.g., incorporating a TiO2 having a primary particle size of from about 100 nm to about 400 nm with a TiO2 having a primary particle size of from about 10 nm to about 50 nm).

Preferred oil compatible colorants are selected from the group consisting of hydrophobically treated talc, mica, magnesium carbonate, calcium carbonate, magnesium silicate, aluminum magnesium silicate, silica, titanium dioxide, zinc oxide, red iron oxide, yellow iron oxide, black iron oxide, titanated mica, iron oxide titanated mica, bismuth oxychloride, and combinations thereof. Most preferred oil compatible colorants are selected from the group consisting of hydrophobically treated titanium, iron oxides, and combinations thereof.

Aqueous compatible colorants include materials that are water dispersible. For instance, lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein. Uncoated inorganic colorants are also suitable aqueous compatible colorants.

Lakes suitable for use in the present invention include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors can also be included in the lipsticks, such as dyes. Suitable examples include Red 6, Red 21, Brown, Russet and Sienna dyes and mixtures thereof.

Preferred aqueous compatible colorants are selected from the group consisting of untreated titanium oxides, untreated iron oxides, hydrophilically-treated titanium oxides, hydrophilically treated iron oxides, Yellow 5 aluminium lake, red 6 barium lake, blue 1 aluminium lake, and combinations thereof. More preferred aqueous compatible colorants are selected from the group consisting of untreated titanium oxides, untreated iron oxides, and combinations thereof.

Dispersants may also be used in conjunction with the colors and pigments of the present invention. Examples of suitable dispersants include, but are not limited to, those described in U.S. Pat. No. 5,688,493.

Emulsifiers

An emulsifier is another essential element of the present invention. The emulsifier may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317–324 (1986. Illustrative nonionic surfactants are alkoxylated compounds based on C10–C22 fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention. Anionic type emulsifiers or surfactants include fatty acid soaps, sodium lauryl sulphate, sodium lauryl ether sulphate, alkyl benzene sulphonate, mono- and di-alkyl acid phosphates and sodium fatty acyl isethionate. Amphoteric emulsifiers or surfactants include such materials as dialkylamine oxide and various types of betaines (such as cocamidopiopyl betaine).

Preferred for use herein are polyoxyalkylene copolymers also known as silicone polyethers. Polymers are described in detail in U.S. Pat. No. 4,268,499. A particularly preferred polyoxyalkylene copolymer is known by its CTFA designation as dimethicones copolyol. A particularly preferred form of dimethicone copolyol is that supplied by Dow Corning as DC5225C.

The overall concentration of the emulsifier can be from 0.01% to about 15%, more preferably from about 0.1% to about 10% of the formulation, even more preferably from 0.1% to about 5% and most preferably from about 0.1% to about 2%, by weight of the composition. Examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El-Nokaly et al.; and Examples of suitable moistures can be found in Cosmetic Bench Reference, pp. 1.22, 1.24–1.26 (1996).

Emulsifying crosslinked organopolysiloxane elastomers can also be used. As used herein "emulsifying" refers to a crosslinked organopolysiloxane elastomer having at least one polyoxyalkylene unit. Emulsifying crosslinked organopolysiloxane elastomers can notably be chosen from the crosslinked polymers described in U.S. Pat. Nos. 5,412,004 (issued May 2, 1995); 5,837,793 (issued Nov. 17, 1998); and 5,811,487 (issued Sep. 22, 1998).

Particularly useful emulsifying elastomers are polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

When included in the compositions of the present invention, the emulsifying crosslinked organopolysiloxane elastomermay be used in the same amounts disclosed above as suitable for other emulsifiers.

Binder

A binder is also an essential component of the claimed composition. The binder acts to provide cohesiveness between the components (e.g., as an emulsion stabilizer) of the claimed composition that tends to improve skin adhesion of the invention (e.g., acts as a film former). Improving the long wear and non-transfer performance of the present compositions is quite desirable. Oil-soluble, oil dispersible, water-soluble, water insoluble, and water dispersible binders can be used in the internal and external phases of the present compositions to give the desired end benefit.

Preferably, the compositions comprise from about 0.01% to about 20%, more preferably, from about 0.1% to about 10%, and most preferably, from about 0.1% to about 5%, by weight of the composition, of the binder.

Suitable binders include:
1) organic silicone resins, fluorinated silicone resins, copolymers of organic silicone resins, e.g., trimethylsiloxysilicate from GE (SR1000), GE's copolymers of silicone resins, e.g., SF1318 (silicone resin and an organic ester of isostearic acid copolymer) and CF1301 (silicone resin and alpha methyl styrene copolymer), Dow Corning's pressure sensitive adhesives—copolymers of silicone resins and various PDMS's (BIO-PSA series); and
2) acrylic and methacrylic polymers and resins, siliconeacrylate type copolymers and fluorinated versions of, including—silicones plus polymer SA70 from 3M, KP545 from Shin-Etsu, alkyl-acrylate copolymers, e.g., KP 561 and 562 from Shin-Etsu;
3) decene/butene copolymer from Collaborative Labs;
4) polyvinyl based materials, e.g., PVP, PVP/VA, including Antaron/Ganex from ISP (PVP/Triacontene copolymer), Luviskol materials from BASF;
5) polyurethanes, e.g., the Polyderm series from Alzo including but not limited to Polyderm PE/PA, Polyderm PPI-SI-WS, Polyderm PPI-GH, Luviset P.U.R. from BASF;
6) polyquaternium materials, e.g., Luviquat series from BASF
7) ammonium acrylates, e.g., Darvan, acrylates copolymers and acrylates/acrylamide copolymers, e.g., Luvimer and Ultrahold series, both available from BASF;
8) styrene based materials; and
9) chitosan and chitosan based materials including cellulose and cellulose-based materials.

Such binders are disclosed for example in the International Cosmetic Ingredient Dictionary and Handbook, Seventh Edition, Vol 2, 1636–1638. A preferred binder for the present invention is ammonium acrylate (commercially available as Darvan®).

Water

The cosmetic compositions of the present invention preferably comprise water at from about 1% to about 95%, preferably from about 5% to about 90%, most preferably from about 25% to about 50%.

Optional Ingredients

Shine Control Agents

Suitable ingredients that improve and/or regulate the condition of the shiny appearance of skin are referred to herein as "shine control agents". Shine control agents may be included in the compositions of the present invention.

A frequent, undesirable condition is "oily skin", which results from the excessive amount of sebum and sweat that is excreted onto the skin. Sebum is an oily mixture, composed principally of squalene, triglycerides, fatty acids and wax esters. Sebum is produced in the sebaceous glands of the skin. Oily skin is associated with a shiny, undesirable appearance and disagreeable tactile sensation. Sweat is predominantly water with trace quantities of dissolved inorganic salts such as sodium chloride and potassium chloride.

Typically, shine control agents are porous in nature. These agents, when applied to the skin provide a reservoir to absorb excess moisture into the pores, hence reducing the visible quantity of moisture on the skin.

Without being limited by theory, it is believed that it is preferable to combine the use of effective porous, absorbent materials with non-absorbing spherical materials. The latter emphasizes the effect of diffuse reflection over problematic specular reflection, causing an optical modification to the skin and hence a reduction in the shiny appearance of the skin. The combination of absorber and non-absorbing spherical particles is preferable because it allows development of a product with optimum shine control as well as providing a product with the best tactile sensory performance.

Suitable shine control agents include, but are not limited to, silicas, magnesium aluminum silicates, talc, sericite and various organic copolymers. Particularly effective shine control agents include silicates or carbonates that are formed by reaction of a carbonate or silicate with the alkali (IA) metals, alkaline earth (IIA) metals, or transition metals, and silicas (silicon dioxide). Preferred shine control agents are selected from the group consisting of calcium silicates, amorphous silicas, calcium carbonates, magnesium carbonates, zinc carbonates, and combinations thereof. Some specific examples of the silicates and carbonates useful in this present invention are more fully explained in Van Nostrand Reinhold's Encyclopedia of Chemistry, $4^{th}$ Ed. pp155, 169, 556, and 849 (1984).

Synthetic versions of the shine control agents, particularly silicates, are preferred. Examples of synthetic silicates useful in the present invention are Hubersorb 250® or Hubersorb 600®, available from J M Huber.

Shine control agents that primarily comprise silicas are preferred over those materials comprising mainly silicates and/or carbonates when used for moisture and shine control. Most preferred silicas are in the form of microspheres and/or ellipsoids, as they have been found to contribute good skin feel characteristics in addition to efficient moisture absorption. Silica ellipsoids useful in the present invention are available from DuPont as ZELEC Sil and Kobo as Silica Shells. Silica microspheres are available from Kobo as MSS-500, MSS500/3, MSS-500H, MSS500/3N, MSS-500N and MSS 500/3N; Presperse as Spheron L1500, Spheron P1500. Fumed versions of silica can also be used with Aerosil from Degussa and Cab-O-Sil from Cabot both being particularly useful.

Amongst the silicate series, magnesium aluminum silicates are useful, in particular Sebumase, available from Miyoshi Kasei.

When silicas, particularly silica ellipsoids and silica microspheres are intended to be the main means for moisture absorption, it is preferred that the absorbent powder comprise from about 1% to about 40%; more preferably from about 1% to about 25%, and most preferably from about 2% to about 10%, by weight of the composition, of silicas.

Starch-based materials may also be used as shine control agents. Useful examples are Natrosorb W and Natrosorb HFW, DryFlo plus and DryFlo AF pure from National Starch and Chemical Company.

Also found to be useful are methacrylate-based polymeric materials. They can be used either in conjunction with a dimethicone copolymer or as methacrylate-based copolymers. Specifically, useful examples are: Microsponge 5640 w. Glycerin, Polytrap 6603 available from Enhanced Derm technologies; DSPCS-12 series and SPCAT-12 from Kobo; Poly-Pore 200 series from Amcol.

Optionally, yet preferably, the compositions of the present invention contain spherical particles having an average particle size diameter of 10 or greater, preferably greater than 15, more preferably greater than 20 microns. The particle diameter is understood to be that of elementary or primary particles.

Preferred spherical particles include, but are not limited, to polymeric particles chosen from the methylsilsesquioxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyerene microspheres such as for example those sold by Dyno Particles under the name Dynospheres, ethylene acrylate copolymer sold by Kobo under the name FloBead EA209 and mixtures thereof. Also found to be useful is Ronasphere LDP from Kobo Inc Preferably the spherical particles are present at a concentration of from about 0% to about 40%, more preferably from about 5% to about 35%, most preferably from about 8% to about 30%.

Skin Conditioning Agent

Optionally, the compositions of the present invention can further comprise a skin-conditioning agent. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin Exfoliants according to the present invention may be selected from C2–C30 alpha-hydroxycarboxylic acids, beta-hydroxycarboxylic acids and salts of these acids. Most preferred are glycolic, lactic and salicylic acids and their ammonium salts.

A wide variety of C2–C30 alpha-hydroxycarboxylic acids may be employed. Suitable examples of which include:
alpha-hydroxyethanoic acid
alpha-hydroxypropanoic acid
alpha-hydroxyhexanoic acid
alpha-hydroxyoctanoic acid
alpha-hydroxydecanoic acid
alpha-hydroxydodecanoic acid
alpha-hydroxytetradecanoic acid
alpha-hydroxyhexadecanoic acid
alpha-hydroxyoctadecanoic acid
alpha-hydroxyeicosanoic acid
alpha-hydroxydocosanoic acid
alpha-hydroxyhexacosanoic acid, and
alpha-hydroxyoctacosanoic acid When the conditioning agent is an emollient it may be selected from hydrocarbons, fatty acids, fatty alcohols and esters. Isononyl isononanoate is the most preferred hydrocarbon type of emollient conditioning agent. Other hydrocarbons that may be employed include mineral oil, polyolefins such as polydecene, and paraffins such as isohexadecane (e.g. Permethyl 99® and Permethyl 101®). Preferably, the compositions of the present invention are substantially free of semi-solid hydrocarbons such as petrolatum, lanolin and lanolin derivatives, sterols (e.g., ethoxylated soya sterols), high molecular weight polybutenes and cocoa butter. By "substantially free," as used herein, means that the concentration of the semi-solid hydrocarbons are preferably less than 10%, more preferably less than 5% most preferably less than 2% and even more preferably 0%. Without being limited by theory, such semi-solid hydrocarbons tend to mask the sensory benefits of the siloxane elastomer compositions such as the non-greasy, light feel of the present invention.

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, safflower oil, cottonseed oil, corn oil, olive oil, cod liver oil, almond oil, avocado oil, palm oil, sesame oil, squalene, Kikui oil and soybean oil.

2. Acetoglyceride esters, such as acetylated monoglycerides.

3. Ethoxylated glycerides, such as ethoxylated glyceryl monostearate.

4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Ether-esters such as fatty acid esters of ethoxylated fatty alcohols.

7. Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

8. Wax esters such as beeswax, spermaceti, myristyl myristate, stearyl stearate.

9. C1–C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 1:3 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Amounts of the skin-conditioning agent may range from about 0% to 30%, preferably from about 1% to about 20%, optimally from about 1% to 10% by weight.

Solidifying Agent

The cosmetic compositions of this invention can contain one or more materials, herein singly or collectively referred to as a "solidifying agent", that are effective to solidify the particular liquid base materials to be used in a cosmetic composition. As used herein, the term "solidify" refers to the physical and/or chemical alteration of the liquid base material so as to form a solid or semi-solid at ambient conditions, i.e., to form a final composition that has a stable physical structure and is deposited on the skin during normal use conditions. As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0.01 to about 90%, more preferably from about 1 to about 50%, even more preferably from about 5% to about 40%, most preferably from about 1% to about 15%.

Suitable solidifying agents include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g., hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40–1.42.

Also useful herein are hydrophilic gelling agents such as the acrylic acid/ethyl acrylate copolymers and the carboxyvinyl polymers sold by the B.F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10–30 Alkyl Acrylate Crosspolymer). Combinations of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646.

Additional examples of suitable gelling agents or gellants can be found in the Cosmetic Bench Reference, p. 1.27.

Further examples of suitable solidifying agents disclosed in the following references: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L.

Waddeam, 3rd Edition (1967), E & F. N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology:, Vol. 24, Kirk-Othmer, 3rd Edition (1979) pp 466–481; U.S. Pat. No. 4,126,679, Davy, et al., issued Nov. 21, 1978; European Patent Specification No. 117,070, May, published Aug. 29, 1984; U.S. Pat. No. 2,900,306, Slater, issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; European Patent Specification No. 24,365 Sampson, et al., published Mar. 4, 1981; and U.S. patent application Ser. No. 630,790, DiPietro, filed Jul. 13, 1984.

Preservatives

Suitable preservatives for compositions of this invention include, but are not limited to, alkyl esters of para-hydroxybenzoic acid, hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium Chloride, and methylbenzethonium chloride. Cosmetic chemists are familiar with appropriate preservatives and routinely choose them to satisfy the preservative challenge test and to provide product stability. Particularly preferred preservatives are disodium EDTA, phenoxyethanol, methyl paraben, ethyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Organic Sunscreens

Compositions of the present invention preferably comprise an organic sunscreen. Suitable sunscreens can have UVA absorbing properties, UVB absorbing properties, and even a mixture thereof. The exact amount of the sunscreen active will vary depending upon the desired Sun Protection Factor, i.e., the "SPF" of the composition as well as the desired level of UVA protection. The compositions of the present invention preferably comprise an SPF of at least 10, preferably at least 15. (SPF is a commonly used measure of photoprotection of a sunscreen against erythema. The SPF is defined as a ratio of the ultraviolet energy required to produce minimal erythema on protected skin to that required to products the same minimal erythema on unprotected skin in the same individual. See Federal Register, 43, No 166, pp. 38206–38269, Aug. 25, 1978). Compositions of the present invention preferably comprise from about 2% to about 20%, more typically from about 4% to about 14%, by weight, of organic sunscreen. Suitable sunscreens include, but are not limited to, those found in the *CTFA International Cosmetic Ingredient Dictionary and Handbook*, 7$^{th}$ *edition*, volume 2 pp. 1672, edited by Wenninger and McEwen (The Cosmetic, Toiletry, and Fragrance Association, Inc., Washington, D. C., 1997).

The compositions of the present invention preferably comprise a UVA absorbing sunscreen actives that absorb UV radiation having a wavelength of from about 320 nm to about 400 nm. Suitable UVA absorbing sunscreen actives are selected from dibenzoylmethane derivatives, anthranilate derivatives such as methylanthranilate and homomethyl, 1-N-acetylanthranilate, and mixtures thereof. Examples of dibenzoylmethane sunscreen actives are described in U.S. Pat. No. 4,387,089 issued to Depolo; and in Sunscreens: Development, Evaluation, and Regulatory Aspects edited by N. J. Lowe and N. A. Shaath, Marcel Dekker, Inc (1990). The UVA absorbing sunscreen active is preferably present in an amount to provide broad-spectrum UVA protection either independently, or in combination with, other UV protective actives that may be present in the composition.

Preferred UVA sunscreen actives are dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'methoxydibenzoylmethane, and mixtures thereof. Preferred dibenzoyl sunscreen actives include those selected from 4-(1,1-dimethylethyl)-4'-methoxydibenzoylmethane, 4-isopropyidibenzoylmethane, and mixtures thereof. A more preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or Avobenzone, is commercially available under the names of Parsol® 1789 from Givaudan Roure (International) S. A. (Basel, Switzerland) and Eusolex® 9020 from Merck & Co., Inc (Whitehouse Station, N.J.). The sunscreen 4-isoproplydibenzoylmethane, which is also known as isopropyldibenzoylmethane, is commercially available from Merck under the name of Eusolex® 8020.

The compositions of the present invention preferably further comprise a UVB sunscreen active that absorbs UV radiation having a wavelength of from about 290 nm to abut 320 nm. The compositions preferably comprise an amount of the UVB sunscreen active that is safe and effective to provide UVB protection either independently, or in combination with, other UV protective actives that may be present in the compositions. The compositions preferably comprise from about 0.1% to abut 16%, more preferably from about 0.1% to about 12%, and most preferably from about 0.5% to about 8% by weight, of UVB absorbing organic sunscreen.

A wide variety of UVB sunscreen actives are suitable for use herein. Nonlimiting examples of such organic sunscreen actives are described in U.S. Pat. No. 5,087,372 issued Feb. 11, 1992 to Haffey et al.; and U.S. Pat. Nos. 5,073,371 and 5,073,372 both issued on Dec. 17, 1991 to Turner et al. Preferred UVB sunscreen actives are selected from 2-ethylhexyl-2-cyano-3,3-diphenylacrylate (referred to as octocrylene), 2-phenyl-benzimidazole-5-sulphonic acid (PBSA), cinnamates and their derivatives such as 2-ethylhexyl-p-methoxycinnamate and octyl-p-methoxycinnamate, TEA salicylate, octyldimethyl PABA, camphor derivatives and their derivatives, and mixtures thereof. Preferred organic sunscreen actives are 2-ethylhexyl-2-cyano-3,3-diphenylacrylate (referred to as octocrylene), 2-phenyl-benzimidazole-5-sulphonic acid (PBSA), octyl-p-methoxycinnamate, and mixtures thereof. Salt and acid neutralised forms of the acidic sunscreens are also useful herein. When organic sunscreen salts, such as PBSA, are used within compositions of the present invention they can disrupt the action of the thickener with the result that the final product may have sub optimal rheology. This can be countered by the addition of higher levels of thickener, fatty alcohols or nonionic surfactants such that the rheology of the final product returns to the desired level.

An agent may also be added to any of the compositions useful in the present invention to stabilise the UVA sunscreen to prevent it from photo-degrading on exposure to UV radiation and thereby maintaining its UVA protection efficacy. Wide ranges of compounds have been cited as providing these stabilising properties and should be chosen to compliment both the UVA sunscreen and the composition as a whole. Suitable stabilising agents include, but are not limited to, those described in U.S. Pat. Nos. 5,972,316; 5,968,485; 5,935,556; 5,827,508 and Patent WO 00/06110. Preferred examples of stabilising agents for use in the present invention include 2-ethylhexyl-2-cyano-3,3-diphenylacrylate (referred to as octocrylene), ethyl-2-cyano-3,3-diphenylacrylate, 2-ethylhexyl-3,3-diphenylacrylate, ethyl-3,3-bis(4-methoxyphenyl)acrylate, and mixtures thereof. 2-ethylhexyl-2-cyano-3,3-diphenylacrylate is most preferred.

An agent may also be added to any of the compositions useful in the present invention to improve the skin substantivity of those compositions, particularly to enhance their resistance to being washed off by water, or rubbed off. A preferred agent that will provide this benefit is a copolymer of ethylene and acrylic acid. Compositions comprising this copolymer are disclosed in U.S. Pat. No. 4,663,157, Brock, issued May 5, 1987.

Inorganic Sunscreens

In addition to the organic sunscreens compositions of the present invention can additionally comprise inorganic physical sunblocks. Nonlimiting examples of suitable physical sunblocks are described in CTFA International Cosmetic Ingredient Dictionary, 6$^{th}$ Edition, 1995, pp. 1026–28 and 1103, Sayre, R. M. et al., "Physical Sunscreens", J. Soc. Cosmet. Chem., Vol 41, no 2, pp. 103–109 (1990). Preferred inorganic physical sunblocks are zinc oxide and titanium dioxide, and mixtures thereof.

When used, the physical sunblocks are present in an amount such that the present compositions are transparent on the skin (i.e. non-whitening), preferably less than or equal to about 5%. When titanium dioxide is used, it can have an anatase, rutile, or amorphous structure. Physical sunblock particles, e.g. titanium dioxide and zinc oxide, can be uncoated or coated with a variety of materials including but not limited to amino acids, aluminum compounds such as alumina, aluminum stearate, aluminum laurate, and the like; carboxylic acids and their salts e.g. stearic acid and its salts; phospholipids such as lecithin; organic silicone compounds; inorganic silicone compounds such as silica and silicates; and mixtures thereof. A preferred titanium dioxide is commercially available from Tayca (Japan) and is distributed by Tri-K Industries (Emerson, N.J.) under the MT microionized series (e.g. MT 100SAS).

The compositions of the present invention preferably comprise from about 0.1% to about 10%, more preferably from about 0.1% to about 4%, and most preferably from about 0.5% to about 2.5%, by weight, of inorganic sunscreen.

Aeration

Optionally and preferably, the compositions of the present invention are aerated. By "aerated" as used herein means the air is incorporated either by hand, mechanical mixing or by using any other form of conventional foaming or whipping instrument technology. Preferably the compositions of the present invention contain at least about 1%, preferably at least about 2%, optimally from about 3 to about 5% air.

Other Optional Ingredients

A variety of additional ingredients can be incorporated into the compositions of the present invention. Nonlimiting examples of these additional ingredients include additional skin care actives such as peptides (e.g., Matrixyl [pentapetide derivative]), farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; sunscreens; anti-acne medicaments (resorcinol, salicylic acid, and the like; antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above-mentioned vitamin $B_3$ compounds can be incorporated as re-crystallized crystals that remain in crystallized form in the composition or as partially solubilize crystals (i.e., some of the crystals are dissolved and some remain in crystalline form in the composition.).

Associated Methods

Applicants have found that the compositions of the present invention are useful in a variety of applications directed to enhancement of mammalian skin. The methods of use for the compositions disclosed and claimed herein include, but are not limited to: 1) methods of providing a natural and radiant appearance of mammalian skin; 2) methods of applying a color cosmetic to skin; 3) methods of providing UV protection to mammalian skin; 4) methods of preventing, retarding, and/or controlling the appearance of oil; 5) methods of modifying the feel and texture of skin; 6) methods of providing even skin tone; and 7) methods of concealing blemishes and/or imperfections in human skin, including acne, age spots, freckles, moles, scars, under eye circles, birth marks, post-inflammatory hyperpigmentation, etc. Each of the methods discussed herein involve topical application of the claimed compositions to skin.

The following examples will more fully illustrate the embodiments of this invention. All parts, percentages and proportions referred to herein and in the appended claims are by weight unless otherwise indicated.

EXAMPLES

The cosmetic products in the following examples illustrate specific embodiments of the cosmetic compositions of the present invention, but are not intended to be limiting thereof. The skilled artisan can undertake other modifications without departing from the spirit and scope of this invention. All exemplified compositions can be prepared by conventional formulation and mixing techniques. Component amounts are listed as weight percents and may exclude minor materials such as diluents, filler, and so forth. The listed formulations, therefore, comprise the listed components and any minor materials associated with such components.

Example I

A liquid foundation of the present invention is prepared as follows:

| Ingredient | Wt % |
|---|---|
| DC9040 cross linked elastomer gel | 30.00 |
| Dimethicone copolyol and cyclopentasiloxane (DC5225C) | 10.00 |
| Cyclomethicone (DC245) | 9.13 |
| Propylparabens | 0.10 |
| Ethylparabens | 0.20 |
| Water | 24.00 |
| Titanium dioxide | 13.50 |
| Iron oxides | 2.50 |
| Glycerin | 10.00 |
| Benzyl alcohol | 0.25 |
| Methylparabens | 0.10 |
| Ammonium polyacrylate (Darvan 821A[1]) | 0.12 |
| Disodium EDTA | 0.10 |

[1]supplied by Vanderbilt

In a suitable vessel, the water, glycerine, disodium EDTA and benzyl alcohol are added and mixed using conventional technology until a clear water phase is achieved. When water phase is clear add methylparabens and mix again until clear. Then add the ammonium polyacrylate, titanium dioxide and iron oxides and mix to disperse. Mix the resultant phase with a Silverson SL2T or similar equipment on high speed (8,000 rpm, standard head) to fully deagglomerate the pigments.

In a separate vessel, add the DC5225C, DC245 and the parabens. This mixture is milled using a Silverson on high speed until homogeneous.

Next, the coloured water phase and the clear, silicone phase are combined and milled using a Silverson on high speed until the water is fully incorporated and an emulsion is formed. The DC9040 is then added and the product is mixed again using a Silverson on high speed. The resulting finished product is then incorporated into the appropriate package.

Example II

A liquid foundation of the present invention is prepared as follows:

| Ingredient | Wt % |
|---|---|
| DC9040 cross linked elastomer gel | 40.00 |
| Dimethicone copolyol cross-polymer (KSG21) | 5.00 |
| Cyclomethicone (DC245) | 17.25 |
| Propylparabens | 0.10 |
| Ethylparabens | 0.20 |
| Water | 15.00 |
| Titanium dioxide | 10.00 |
| Iron oxides | 1.50 |
| Glycerin | 10.00 |
| Benzyl alcohol | 0.25 |
| Methylparabens | 0.10 |
| PVP (Lukiskol K90) | 0.50 |
| Disodium EDTA | 0.10 |

In a suitable vessel, the water, glycerine, disodium EDTA and benzyl alcohol are added and mixed using conventional technology until a clear water phase is achieved. When water phase is clear add methylparabens and mix again until clear. Then add the PVP, titanium dioxide and iron oxides and mix to disperse. Mix the resultant phase with a Silverson SL2T or similar equipment on high speed (8,000 rpm, standard head) to fully deagglomerate the pigments.

In a separate vessel, add the KSG21, DC245 and the parabens. This mixture is milled using a Silverson on high speed until homogeneous.

Next, the coloured water phase and the clear, silicone phase are combined and milled using a Silverson on high speed until the water is fully incorporated and an emulsion is formed. The DC9040 is then added and the product is mixed again using a Silverson on high speed. The resulting finished product is then incorporated into the appropriate package.

Example III

A liquid foundation of the present invention is prepared as follows:

| Ingredient | Wt % |
|---|---|
| DC9040 cross linked elastomer gel | 40.00 |
| Dimethicone copolyol cross-polymer (KSG21) | 5.00 |
| Cyclomethicone (DC245) | 18.40 |
| Propylparabens | 0.10 |
| Ethylparabens | 0.20 |
| Water | 20.00 |
| Titanium dioxide | 9.00 |
| Iron oxides | 1.50 |
| Glycerin | 5.00 |
| Benzyl alcohol | 0.25 |
| Methylparabens | 0.10 |
| Polacrylamide (Sepigel 305) | 0.35 |
| Disodium EDTA | 0.10 |

In a suitable vessel, the water, glycerine, disodium EDTA and benzyl alcohol are added and mixed using conventional technology until a clear water phase is achieved. When water phase is clear add methylparabens and mix again until clear. Then add the titanium dioxide and iron oxides and mix to disperse. Mix the resultant phase with a Silverson SL2T or similar equipment on high speed (8,000 rpm, standard head) to fully deagglomerate the pigments. Finally, add the Sepigel to the water phase with the mixer operational on high speed.

In a separate vessel, add the KSG21, DC245 and the parabens. This mixture is milled using a Silverson on high speed until homogeneous. Next, the coloured water phase and the clear silicone phase are combined and milled using a Silverson on high speed until the water is fully incorporated and an emulsion is formed. The DC9040 is then added and the product is mixed again using a Silverson on high speed. The resulting finished product is then incorporated into the appropriate package.

Example IV

A liquid foundation of the present invention is prepared as follows:

| Ingredient | Wt % |
| --- | --- |
| DC9040 cross linked elastomer gel | 40.00 |
| Dimethicone copolyol cross-polymer (KSG21) | 5.00 |
| Cyclomethicone (DC245) | 18.65 |
| Propylparabens | 0.10 |
| Ethylparabens | 0.20 |
| Water | 20.00 |
| Titanium dioxide | 9.00 |
| Iron oxides | 1.50 |
| Glycerin | 5.00 |
| Benzyl alcohol | 0.25 |
| Methylparabens | 0.10 |
| Ammonium polyacrylate (Darvan 821A) | 0.10 |
| Disodium EDTA | 0.10 |

In a suitable vessel, the water, glycerine, disodium EDTA and benzyl alcohol are added and mixed using conventional technology until a clear water phase is achieved. When water phase is clear add methylparabens and mix again until clear. Then add the Darvan titanium dioxide and iron oxides and mix to disperse. Mix the resultant phase with a Silverson SL2T or similar equipment on high speed (8,000 rpm, standard head) to fully deagglomerate the pigments.

In a separate vessel, add the KSG21, DC245 and the parabens. This mixture is milled using a Silverson on high speed until homogeneous.

Next, the coloured clear water phase and the clear, silicone phase are combined and milled using a Silverson on high speed until the water is fully incorporated and an emulsion is formed. The DC9040 is then added and the product is mixed again using a Silverson on high speed. The resulting finished product is then incorporated into the appropriate package.

Example V

A liquid foundation with SPF of the present invention is prepared as follows:

| Ingredient | Wt % |
| --- | --- |
| DC9040 cross linked elastomer gel | 25.00 |
| Dimethicone copolyol and cyclopentasiloxane (DC5225C) | 10.00 |
| Octylmethoxycinnimate (Parsol MCX) | 4.00 |
| Cyclomethicone (DC245) | 8.13 |
| Propylparabens | 0.10 |
| Ethylparabens | 0.20 |
| Water | 24.00 |
| Niacinamide | 2.00 |
| Titanium dioxide | 13.50 |
| Iron oxides | 2.50 |
| Glycerin | 10.00 |
| Benzyl alcohol | 0.25 |
| Methylparabens | 0.10 |
| Ammonium polyacrylate (Darvan 821A[1]) | 0.12 |
| Disodium EDTA | 0.10 |

In a suitable vessel, the water, glycerine, niacinamide, disodium EDTA and benzyl alcohol are added and mixed using conventional technology until a clear water phase is achieved. When water phase is clear add methylparabens and mix again until clear. Then add the ammonium polyacrylate, titanium dioxide and iron oxides and mix to disperse. Mix the resultant phase with a Silverson SL2T or similar equipment on high speed (8,000 rpm, standard head) to fully deagglomerate the pigments.

In a separate vessel, add the DC5225C, DC245, Parsol and the parabens. This mixture is milled using a Silverson on high speed until homogeneous.

Next, the coloured water phase and the clear silicone phase are combined and milled using a Silverson on high speed until the water is fully incorporated and an emulsion is formed. The DC9040 is then added and the product is mixed again using a Silverson on high speed. The resulting finished product is then incorporated into the appropriate package.

Example VI

A solid foundation of the present invention is prepared as follows:

| Ingredient | Wt % |
| --- | --- |
| Silicone elastomer suspension in water (DC9509) | 10.00 |
| Water | 43.50 |
| Glycerin | 10.00 |
| Benzyl alcohol | 0.25 |
| Methylparabens | 0.10 |
| Disodium EDTA | 0.10 |
| Cetearyl glucoside and cetyl alcohol (Emulgade PL68-50) | 4.00 |
| Cyclomethicone (DC245) | 15.25 |
| Titanium dioxide - silicone coated | 14.00 |
| Iron oxides - silicone coated | 2.50 |
| Propylparabens | 0.10 |
| Ethylparabens | 0.20 |

In a suitable vessel, the water, glycerine, disodium EDTA and benzyl alcohol are added and mixed using conventional technology until a clear water phase is achieved. When water phase is clear add methylparabens and mix again until clear. Then heat the water phase up to 70 deg C. whilst agitating.

In a separate vessel, mix the Emulgade and DC245 on a low shear mixer and heat up to 65 degC. until the Emulgade has melted. Then add the titanium and iron oxides and parabens and mill this mixture using a Silverson on high speed until homogeneous.

Next, the clear water phase and the colored silicone phase are combined and milled using a Silverson on high speed until the silicone is fully incorporated and an emulsion is formed. The DC9509 is then added and the product is mixed again using a Silverson on high speed. The resulting finished product is then incorporated into the appropriate package.

What is claimed is:

1. A cosmetic composition comprising an oil-in-water emulsion that further comprises:
    a) a continuous aqueous phase comprising:
        1) from about 0.1% to about 10%, by weight of the composition, of a non-emulsifying crosslinked siloxane elastomer swelled in a non-polar solvent;
    b) a dispersed oil phase comprising:
        1) from about 1% to about 25%, by weight of the composition, of an oil compatible colorant; and
        2) from about 0.01% to about 20%, by weight of the composition, of a binder; and
    c) from about 0.01% to about 15%, by weight of the composition, of an emulsifier.

2. The cosmetic composition of claim 1 wherein the composition further comprises a skin conditioning agent that is selected from the group consisting of humectants, exfoliants, emollients and mixtures thereof.

3. The cosmetic composition of claim 2 wherein the humectant is selected from the group consisting of propylene glycol, dipropylene glycol, polypropylene glycol, polyethylene glycol, sorbitol, hydroxypropyl sorbitol, hexylene glycol, glycerin, 1,3-butylene glycol, 1,2,6-hexanetriol, ethoxylated glycerin, propoxylated glycerin and mixtures thereof.

4. The cosmetic composition of claim 3 wherein the skin-conditioning agent is an emollient selected from the group consisting of hydrocarbons, fatty acids, fatty alcohols and esters, and combinations thereof.

5. The cosmetic composition of claim 1 wherein the emulsifier is selected from the group consisting of polyoxyalkylene copolymers, emulsifying crosslinked siloxane elastomers, and combinations thereof.

6. The cosmetic composition of claim 1 wherein said oil compatible colorant is selected from the group consisting of hydrophobically treated talc, mica, magnesium carbonate, calcium carbonate, magnesium silicate, aluminum magnesium silicate, silica, titanium dioxide, zinc oxide, red iron oxide, yellow iron oxide, black iron oxide, titanated mica, iron oxide titanated mica, bismuth oxychloride, and combinations thereof.

7. The cosmetic composition of claim 1 in a product form selected from the group consisting of foundations, mascaras, concealers, eyeliners, brow colors, eye shadows, blushers, lip paints, lip glosses, lipsticks, and combinations thereof.

8. The cosmetic composition of claim 1 wherein said composition further comprises an active selected from the group consisting of a sunscreen active, a shine control agent, and combinations thereof.

9. A method of providing a natural and radiant appearance to mammalian skin wherein said method comprises the step of topically applying the composition of claim 1 to mammalian skin.

10. A method of providing UV protection to mammalian skin wherein said method comprises the step of topically applying the composition of claim 1 to mammalian skin.

* * * * *